United States Patent
Nomura et al.

[19]

[11] Patent Number: 6,053,035
[45] Date of Patent: Apr. 25, 2000

[54] MATERIAL EVALUATION METHOD

[76] Inventors: Satoshi Nomura; Shuji Takamatsu; Motoi Nakao, all of c/o Horiba, Ltd., 2, Miyanohigashi-machi, Kissyoin, Minami-ku, Kyoto, Japan

[21] Appl. No.: 09/071,332

[22] Filed: May 1, 1998

[30] Foreign Application Priority Data

May 10, 1997 [JP] Japan .................................... 9-136192

[51] Int. Cl.[7] .......................... G01N 17/00; G01N 27/26
[52] U.S. Cl. ............................................ 73/86; 205/777.5
[58] Field of Search ............................ 205/787.5, 777.5; 422/82.04; 324/438; 204/406, 407, 426; 73/86, 866

[56] References Cited

U.S. PATENT DOCUMENTS

| | | | |
|---|---|---|---|
| H1563 | 7/1996 | Snyder et al. | 435/7.32 |
| 4,591,550 | 5/1986 | Hafeman et al. | 205/777.5 |
| 4,963,815 | 10/1990 | Hafeman | 205/777.5 |
| 5,200,051 | 4/1993 | Cozzette et al. | 204/403 |
| 5,348,627 | 9/1994 | Propst et al. | 205/655 |
| 5,489,515 | 2/1996 | Hatschek et al. | 435/29 |
| 5,500,188 | 3/1996 | Hafeman et al. | 422/82.02 |
| 5,567,302 | 10/1996 | Song et al. | |
| 5,837,446 | 11/1998 | Cozzette et al. | 435/6 |

FOREIGN PATENT DOCUMENTS 0 750 195 A1   12/1996   European Pat. Off. .

OTHER PUBLICATIONS

"Scanning–laser–beam semiconductor pH–imaging sensor," vol. B20, No. 2/03, Jun. 1, 1994, pp. 119–223.

"Patent Abstracts of Japan," vol. 096, No. 011, Nov. 29, 1996 & JP 08 193937 (Hitachi Ltd), Jul. 30, 1996.

"The Light–Addressable Potentiometric Sensor: Principles and Biological Applications," John C. Owicki, et al., *Annual Review of Biophysics and Biomolecular Structure*, vol. 23, 1994, Palo Alto, CA, pp. 87–113, XP002073025.

European Search Report, EP 98 10 8468, Munich, Jul. 29, 1998.

Lundstrom et al, 1991. Artificial olfactory images from a chemical sensor using a light–pulse technique. *Nature* 352:47–50.

*Primary Examiner*—Daniel S. Larkin
*Assistant Examiner*—Jay L. Politzer
*Attorney, Agent, or Firm*—Oppenheimer Wolff & Donnelly, LLP

[57] ABSTRACT

A method for evaluating material is carried out by making current measurements in an electrolyte positioned between a sensor and a material to be evaluated. The sensor has a substrate and a sensor surface. A light source is disposed in a spaced relationship with the substrate of the sensor. An electrolyte such as a gas or a solution is positioned to contact the sensor surface, and a material to be evaluated is positioned to contact the electrolyte, such that the electrolyte is positioned between the sensor and the material to be evaluated. A change in a property of the electrolyte, for example, pH, is caused by irradiating the sensor with the light beam. By generating a current in the substrate and then measuring the current, the pH of the electrolyte may be determined.

10 Claims, 5 Drawing Sheets

1

MATERIAL EVALUATION METHOD

BACKGROUND OF THE INVENTION

1. Field of the Invention

The present invention relates to a method for evaluating various materials including organic materials such as plastics as well as inorganic materials such as cement or metal materials.

2. Description of the Prior Art

For a method to evaluate the properties of substances or materials such as uniformity, corrosion resistance, degree of coating, strength, etc., weight change of the whole material or concentration change of dissolved substance of the whole liquid when the material is immersed in the liquid are measured.

The measurements are known as bulk measurements, which require a certain size of lump as a substance to be measured. At the same time, when the concentration, e.g., is measured, highly sophisticated high-sensitivity analysis technique is required. There also has been an inconvenience in that it takes a long time to generate a concentration change or weight change that can be detected by the existing analytical techniques.

SUMMARY OF THE INVENTION

The present invention has been achieved with the above-mentioned matters taken into account, and it is the object of this invention to provide a method for evaluating materials that can evaluate the properties of various materials easily and quickly, as well as accurately and reliably, even if there exists only a small amount of material.

To achieve this objective, the method for evaluating materials according to this invention is designed to provide a solution or gas in such a manner to come in contact with a sensor surface of a scanning type two-dimensional concentration distribution measuring equipment which has a sensor surface on one surface of a semiconductor substrate and irradiates the semiconductor substrate with a light beam. The equipment is designed to detect subtle changes in distribution of substance concentration or property parameters induced in the solution or gas when the material to be evaluated is mounted in such a manner to make contact with the solution or gas.

For example, when a metal material is immersed in a suitable electrolyte solution, an electrochemical reaction occurs at the portion where corrosion or depletion due to corrosion is formed. Consequently, the pH of the solution in the vicinity greatly varies as compared with other areas. It is possible to evaluate the metal material by analyzing this localized change of pH. However, because the present electrochemical measuring method measures the average information of the applicable portion, it is unable to analyze the localized phenomena in detail. A conventional scanning pH electrode method for measuring two-dimensional distribution of pH has an extremely slow response speed of the electrode and big restriction in time resolution or space resolution from the viewpoint of electrode size.

As against this, the material evaluation method according to this invention can detect changes of pH distribution induced in the solution by filling the cell formed with, for example, resin material with the electrolyte solution (for example, artificial seawater), holding the metal material to be evaluated in this solution with about 1 mm clearance provided from the sensor surface, inserting a counter electrode and a reference electrode in the solution, and applying a specified bias voltage.

By the material evaluation method according to this invention, it is possible to evaluate various materials more easily and more quickly than with conventional methods. Since the various materials can be evaluated directly in conformity with the real substance, the materials can be evaluated in good accuracy and reliably.

The light scanning type two-dimensional concentration distribution measuring equipment used in the material evaluation method may be designed to have an upper portion of the sensor surface open, but may be configured to mount a lid above the sensor surface in such a manner to cover it, to place the material to be evaluated between the lid and the sensor surface, to introduce the solution or gas to bring it in contact with the sensor surface and the evaluated material from one side of the sensor surface, and to discharge it from the other side of the sensor surface.

DETAILED DESCRIPTION OF THE PREFERRED EMBODIMENTS

Figure 1:
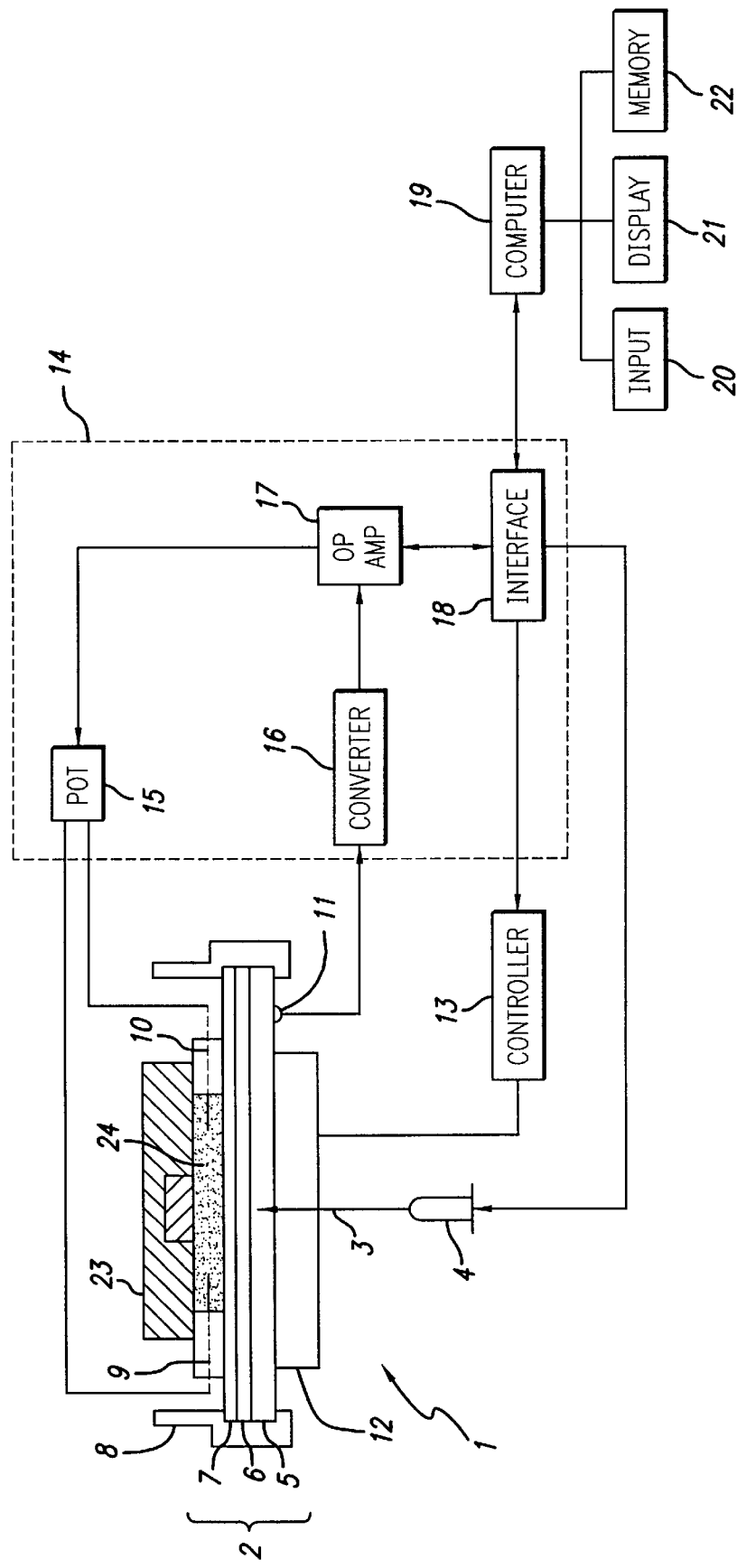
FIG. 1 is a schematic view showing an overall configuration of equipment used for a material evaluation method in accordance with a first embodiment of the invention.
Figure 2:
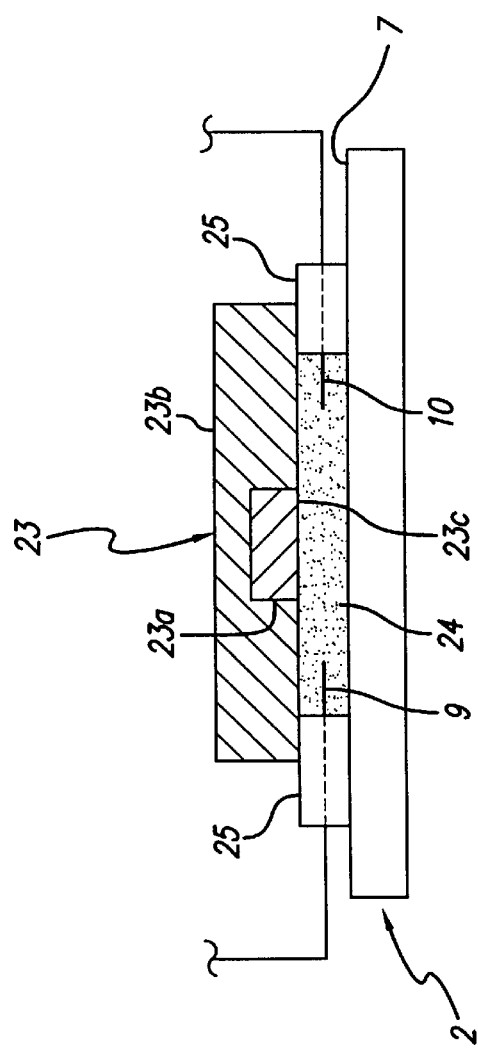
FIG. 2 is an enlarged cross-sectional view showing a portion of the equipment.

Referring now to the drawings, there are shown preferred embodiments of this invention. FIG. 1 through FIG. 3 show a first embodiment. First of all, scanning-type two-dimensional concentration distribution measuring equipment used for material evaluation methods of the invention will be described referring to FIG. 1.

In FIG. 1, numeral 1 designates measuring equipment which includes a sensor portion 2 and a light beam irradiating portion 4 for irradiating the sensor portion with a light beam 3.

The sensor portion 2 is built by successively forming a $SiO_2$ layer 6 and a $Si_3N_4$ layer 7 on one surface (i.e., a top surface in the illustrated example) of a substrate 5 made from a semiconductor, such as silicon, by, for example, thermal oxidation, chemical vapor deposition, etc. The sensor portion 2 is designed to be formed to respond to hydrogen ions. Numeral 8 is a cell which contains the sensor surface (in this case, the $Si_3N_4$ layer 7) of the sensor portion 2. The cell 8 also serves as a sensor holder mounted in such a manner to face the sensor surface. The cell 8 is made from resin material or other suitable materials, and is configured to accommodate the solution or gel in contact with sensor surface 7. Sensor surface 7 is measured a few centimeters in all directions.

Numerals 9 and 10 are a counter electrode and a reference electrode, respectively, which are mounted in such a manner to face sensor surface 7. Electrodes 9 and 10 are connected to a potentiostat 15. Numeral 11 is an ohmic electrode for removing current signals to be mounted to semiconductor substrate 5. Electrode 11 is connected to the potentiostat 15 via a current-voltage converter 16 and an operational amplifier circuit 17, which will be later discussed.

Numeral 12 is equipment for scanning the sensor portion 2 in two-dimensional directions, that is, an X direction (which is horizontal in the illustrated example) and a Y direction (which is perpendicular to the paper in the illustrated example). Scanning equipment 12 is controlled by a signal from a scanning controller 13.

The beam irradiating portion 4 includes, for example, laser beam sources, and is located on the bottom surface side (a side opposite to sensor surface 7) of the semiconductor substrate 5. The beam irradiating portion 4 emits an intermittent beam in response to the control signal of computer 19 via interface board 18. At the same time, beam irradiating portion 4 is designed to irradiate sensor portion 2 with light beam 3 adjusted to have a beam diameter suited for semiconductor substrate 5 of sensor portion 2 scanned in the two-dimensional directions by sensor portion scanning equipment 12.

Numeral 14 is a control box for controlling the measuring equipment 1. Control box 14 includes a potentiostat 15 for applying suitable bias voltage to semiconductor substrate 5, a current-voltage converter 16 for converting the current signal taken out from ohmic electrode 11 formed in semiconductor substrate 5 into the voltage signal, an operational amplifier circuit 17 to which signals from the current-voltage converter 16 are input, and an interface board 18 for transmitting and receiving signals to and from the operational amplifier circuit 17 or for outputting control signals to scanning controller 13.

Numeral 19 is a computer implemented as a controller and processing unit for carrying out various controls and computations and may be equipped with image processing capabilities. Numeral 20 is an input unit such as a keyboard; numeral 21 is a display unit such as a color display; and numeral 22 is a memory unit.

The material evaluation method using the light scanning-type two-dimensional concentration distribution measuring equipment of the above configuration is described referring to FIG. 2 and FIG. 3. The measurement of corrosion formed in the vicinity of the joint between magnetic stainless steel and Ag (silver) alloy is used as an example.

In FIG. 2, numeral 23 is metal material formed by joining magnetic stainless steel and Ag (silver) alloy. Magnetic stainless steel 23a and Ag alloy 23b are joined together to be flush at a joint 23c side. This metal material 23 is immersed in a 0.9% physiological salt solution for, e.g., about 3 weeks. Numeral 24 is a gel-form agar film mounted to come in contact with sensor surface 7. The agar film 24 is prepared by adding 1.5% agar to the 0.9% physiological salt solution with subsequent heating and solidifying to yield a thickness of about 0.5 mm–1 mm.

As shown in FIG. 2, gelled solution 24 is placed on sensor surface 7. The metal material 23 is placed on this gelled solution 24 in such a manner that joint 23c (i.e., the portion subject to the evaluation) between the magnetic stainless steel 23a and the Ag alloy 23b comes in contact with gelled solution 24. Numeral 25 is a spacer made of silicon in thickness similar to that of gelled solution 24 and is arranged around gelled solution 24.

When metal material 23 is placed on gelled solution 24 in such a manner that the lower surface side containing the portion subject to the evaluation 23c is parallel to sensor surface 7 as described above, a change in pH occurs in gelled solution 24. This pH change can only be measured in the tiny area and is the change that can be detected by the light scanning-type two-dimensional concentration distribution measuring equipment.

The counter electrode 9 and reference electrode 10 are mounted in such a manner that they penetrate spacer 25 and reach gelled solution 24. The DC voltage from potentiostat 15 is applied across reference electrode 10 and ohmic electrode 11 so that a depletion layer is generated in semiconductor substrate 5. A specified bias voltage is thus applied to semiconductor substrate 5. By intermittently irradiating semiconductor substrate 5 with light beam 3 at specified intervals (for example, 5 kHz) under this condition, AC photoelectric current is generated on semiconductor substrate 5. This intermittent irradiation of light beam 3 is carried out by inputting a control signal from computer 19 via interface board 18. The photoelectric current is the value reflecting the pH in gelled solution 24 in contact with sensor surface 7 at the point opposite to the irradiation point of semiconductor substrate 5. By measuring the value of the current, the pH at this portion can be determined.

In addition, by moving the sensor portion 2 in X and Y directions by sensor portion scanning equipment 12, semiconductor substrate 5 is irradiated in such a manner that probe beam 3 is scanned in two directions, and a two-dimensional image that represents the pH is displayed on the screen of display unit 21 by the position signals (X, Y) at gelled solution 24 and the AC photoelectric current observed at the spot.

The image display is carried out, for example, in the following manner. For example, let the image size be 1 cm×2 cm and the pixel size be 100 $\mu$m; then, the pH at each measuring point (100×200) is arranged in correspondence with the positional coordinate of the measuring point. The arranged values are displayed as a chemical image similar to, for example, STM (scanning-type tunnel microscope) image in correspondence with the gray scale or color scale.

FIG. 3 shows one example of a chemical image obtained by measuring the changes with time of the pH attributed to corrosion at joint 23b, which is the portion subject to the evaluation of the metal sample 23. The pH of the background is 6.3. Image A in FIG. 3 shows the pH distribution in the vicinity of joint portion 23c right after the measurement is started. Thereafter, images B to H show the pH distribution when the pH is measured at intervals of 4 to 6 minutes, while image H shows the condition 30 minutes after the measurement is started.

As clear from the description above, the light scanning-type two-dimensional concentration distribution measuring equipment used in the material evaluation method according to this invention can accurately and quickly evaluate the subtle pH change in the tiny area, and is able to image-process and display the change as a two-dimensional image on the screen of display unit 21. Consequently, by the material evaluation method according to this invention, it is possible to evaluate the material more easily and more quickly than by conventional methods. Since it is possible to evaluate the material directly in conformity with the real substance, the material can be evaluated with high accuracy and high reliability.

In the above-mentioned embodiment, substance 24 in which the physiological salt water is gelled is placed on sensor surface 7. Alternatively, in place of this, it is allowed to store the physiological salt water in cell 8 and bring it in contact with sensor surface 7. At the same time, metal material 23 may be immersed in this physiological salt water at the portion to be evaluated. In such event, the portion 23c to be evaluated of metal material 23 must be kept away by a specified distance (for example, about 1 mm) from sensor surface 7.

Figure 4:
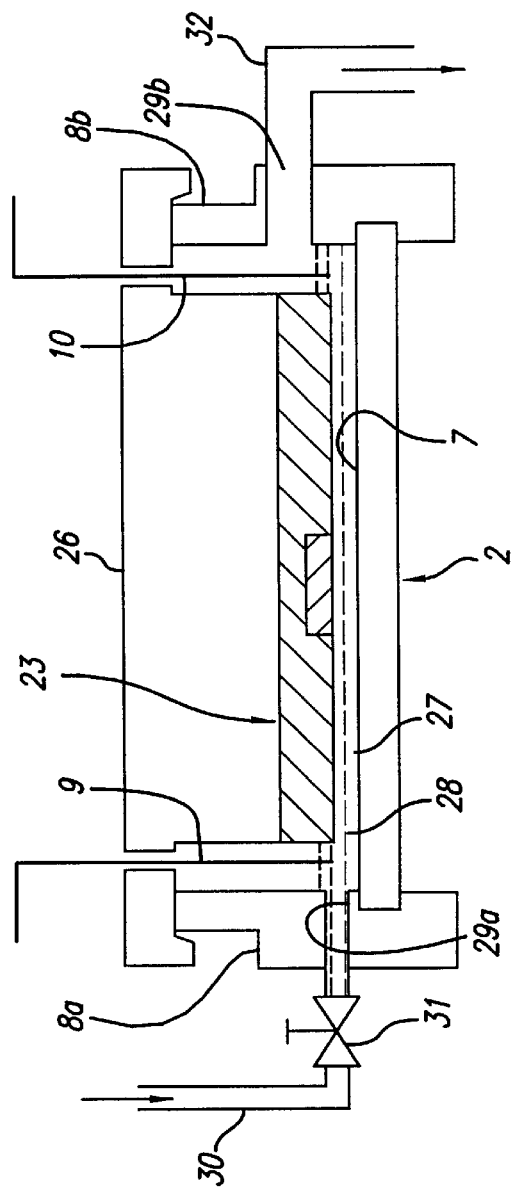
FIG. 4 is a cross-sectional view schematically showing a portion of the equipment used for the material evaluation method in accordance with a second embodiment of the invention.
Figure 3I:
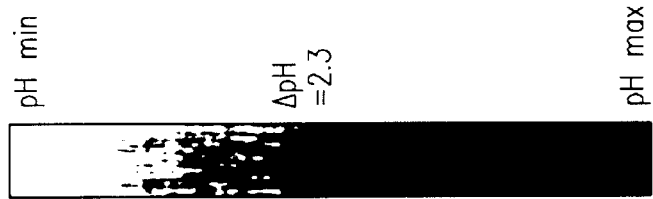
FIG. 3 illustrates various views of one example of data obtained by the material evaluation method of the invention.
Figure 3D:
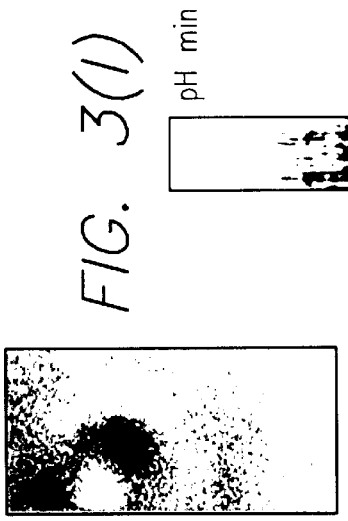
Figure 3C:
Figure 3B:
Figure 3A:
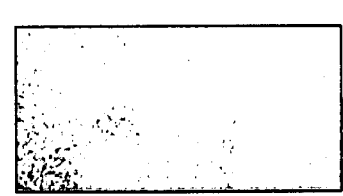
Figure 3H:
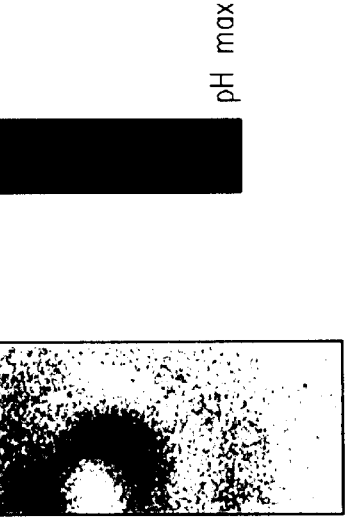
Figure 3G:
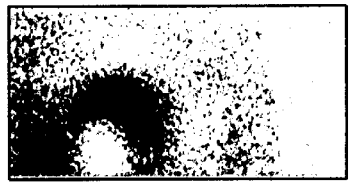
Figure 3F:
Figure 3E:

In the above-mentioned embodiment, the upper portion of sensor surface 7 is held open. Alternatively, it may be configured as shown in FIG. 4. That is, FIG. 4 shows a second embodiment of the invention, in which numeral 26 is a lid which is removably attached above the sensor surface to cover the upper portion of sensor surface 7. Lid 26 is designed to removably hold metal material 23, the material subject to evaluation, below it. In this event, a clearance 27 of about 1 mm should be provided between the bottom surface of metal material 23 and sensor surface 7.

Side walls 8a, 8b of cell 8 are erectly mounted around sensor surface 7, and include inlet port 29a and outlet port 29b of physiological salt water 28. A switching valve 31 is mounted to a pipe 30 connected to inlet port 29a, the upstream side of which is connected to the psychological salt water source via a pump (not illustrated). Pipe 32 connected to outlet port 29b is connected to the discharge port.

In the embodiment shown in FIG. 4, sensor surface 7 is covered with lid 26 under which metal material 23 mounted. Under this condition, physiological salt water 28 is allowed to pass clearance 27 between the bottom surface of metal material 23 and sensor surface 7. After a suitable time or days have passed, the flow of physiological salt water 28 is stopped, and the subtle pH change induced in the stationary physiological salt water 28 can be measured by the light scanning-type two-dimensional concentration distribution measuring equipment. According to this embodiment, pretreatment of metal material 23 to be evaluated and pH measurement for evaluation can be carried out on the optical scanning type two-dimensional concentration distribution measuring equipment, requiring only a small space for the treatment and operation and achieving easy handling.

Figure 5:
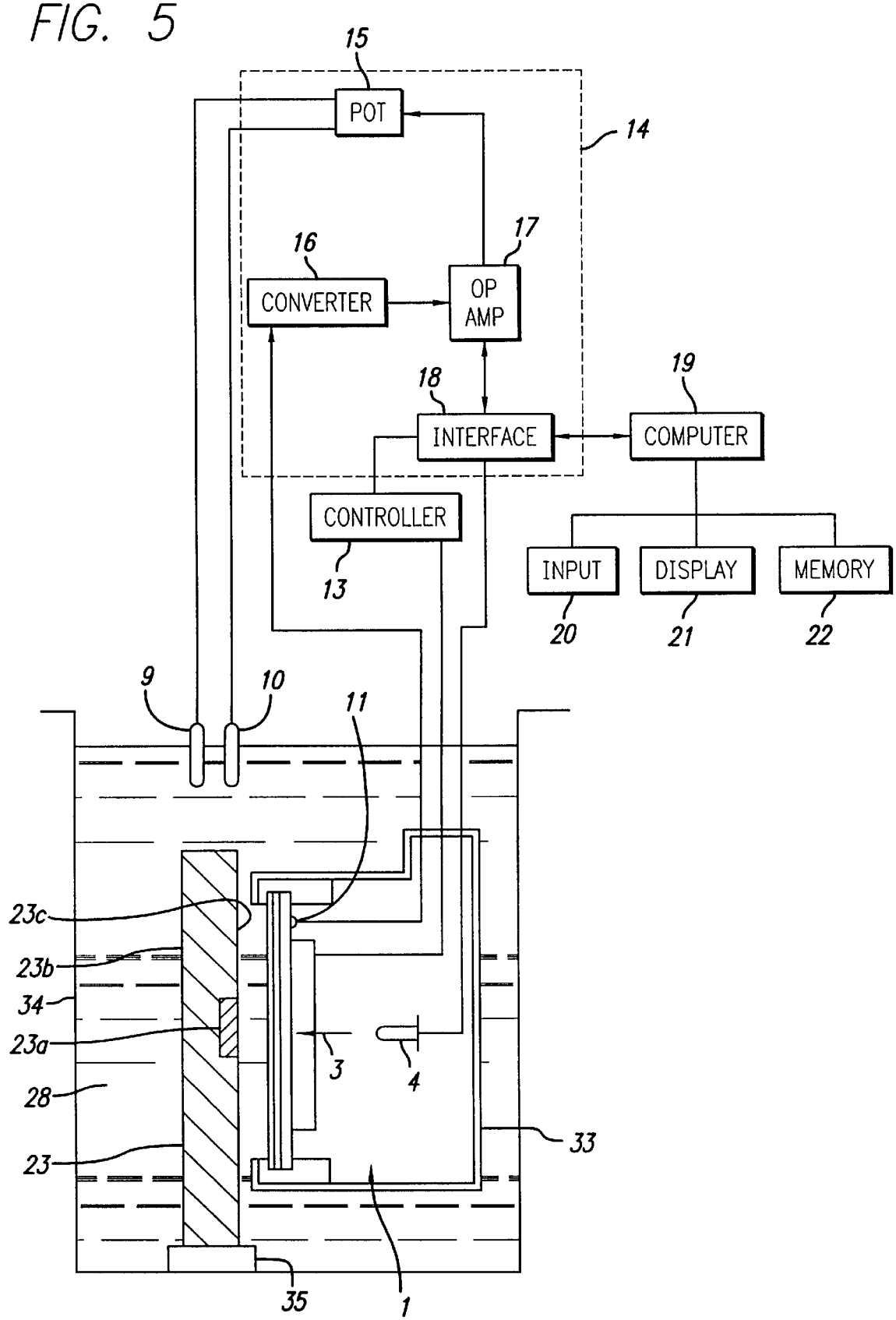
FIG. 5 is a schematic view showing an overall configuration of the equipment used for the material evaluation method in accordance with a third embodiment of the invention.

FIG. 5 shows a third embodiment according to this invention. The light scanning-type two-dimensional concentration distribution measuring equipment, except for sensor surface 7 of the measuring equipment 1, is covered with polyimide film or other insulation material 33 with excellent water repellence and insulation. In a suitable container 34, physiological salt water 28 is contained. In the physiological salt water 28, metal material 23 to be evaluated is placed while held on support 35. Sensor surface 7 is positioned with a suitable spacing (about a few mm) remaining between evaluated surface 23c of metal material 23 and the measuring equipment 1 when completely immersed in physiological salt water 28. In this case, counter electrode 9 and reference electrode 10 are placed in such a manner to be immersed in physiological salt water 28.

In the two-dimensional ion concentration measuring equipment to be used in each embodiment described above, reference electrode 10 may be omitted, and bias voltage may be applied via counter electrode 9. However, bias voltage is able to be applied more stably to semiconductor substrate 5 when reference electrode 10 is provided.

In place of moving sensor portion 2 in the X and Y directions in each light scanning type two-dimensional concentration distribution measuring equipment, an optical portion scanning equipment may be installed at beam-irradiating portion 4. The beam irradiating portion 4 may thus be moved in the X and Y directions. In addition, a light beam scanning equipment may be installed between the light irradiating portion 4 and sensor portion 2, and light beam 3 may be moved in the X and Y directions.

In addition, in the light scanning type two-dimensional concentration distribution measuring equipment, light beam 3 by beam irradiating portion 4 is designed to be irradiated from the side opposite to sensor surface 7 of semiconductor substrate 5. Alternatively, it may be irradiated from sensor surface 7 side. For the light irradiating portion 4, a light irradiating portion incorporated in semiconductor substrate 5 may be adopted as shown in, for example, Japanese Patent Application No. Hei 7-39114.

Furthermore, in each of the above-mentioned embodiments, all are designed to analyze the two-dimensional distribution condition of proton (pH) and to evaluate material 23 based on this information. Alternatively, cell 8 may be filled with other solutions, for example, a KCl solution, and the two-dimensional distribution condition of the potassium ion or chloride ion contained in the solution may be analyzed. Based on this, material 23 may be evaluated. In this event, sensor surface 7 of the light scanning type two-dimensional concentration distribution measuring equipment must be modified with the substance which responds to the potassium ion or chloride ion, respectively. That is, examples of substances responding to the potassium ion include valinomycin or crown ether, and examples of substances responding to the chloride ion include the quaternary ammonium salt. Sensor surface 7 is modified with these responding substances.

However, the material evaluation method described above is to observe changes of the pH distribution in gel 24 or solution 28 with which material 23 to be evaluated is brought in contact. Based on this information, material 23 is evaluated, but material 23 to be evaluated may be brought in contact with gas, and changes of the pH distribution in this gas may be observed. This configuration will be described below as the fourth embodiment of the invention.

Figure 6:
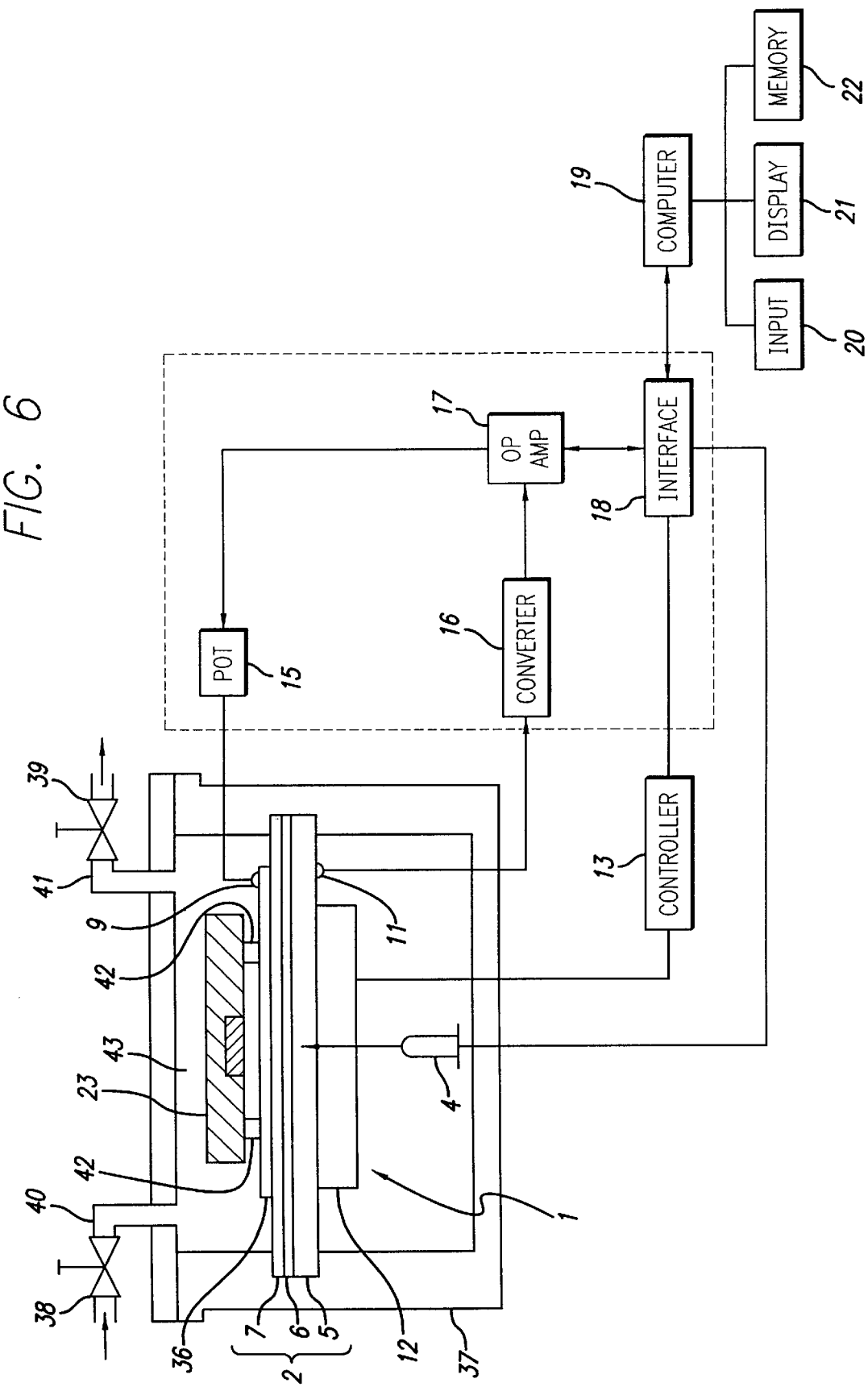
FIG. 6 is a schematic view showing an overall configuration of the equipment used for the material evaluation method in accordance with a fourth embodiment of the invention.

FIG. 6 shows the fourth embodiment according to this invention, and the light scanning type two-dimensional concentration distribution measuring equipment shown in FIG. 6 has a gas-sensitive film 36 formed as the gas sensor surface comprising $SnO_2$ (tin oxide) or Pd (palladium) on the top of sensor surface 7 of measuring equipment proper 1. To this gas-sensitive film 36, counter electrode 9 is connected. In this case, reference electrode 10 is not installed. The measuring equipment proper 1 is contained in a hermetically sealed gas chamber 37. To this gas chamber 37, gas introducing pipes 40 and 41 equipped with switching valves 38 and 39, respectively, are connected. Gas introducing pipe 40 is connected to the gas supplying source (not illustrated) and gas discharging pipe 41 is connected to the discharge port (not illustrated).

To carry out evaluation of, for example, metal material 23 using the light scanning type two-dimensional concentration distribution measuring equipment of the above-mentioned configuration, spacers 42 made of silicon are arranged at suitable intervals on the top surface of gas-sensitive film 36, and metal material 23 is held in parallel with an about 1 mm clearance provided from gas-sensitive film 36. Switching valve 38 on the gas introducing side is opened and switching valve 39 on the gas discharging side is closed to supply either gas 43 of, for example, HCl (hydrogen chloride), $H_2$ (hydrogen gas), or $N_2$ (nitrogen gas) to fill gas chamber 37, and switching valve 38 is closed. This gas 43 comes in contact with surface 23c subject to evaluation of metal material 23 and gas-sensitive film 36, and changes occur in the gas concentration.

The changes of the gas concentration are detected by gas-sensitive film 36, and the two-dimensional distribution of the gas concentration is able to be obtained by irradiating semiconductor substrate 5 with light beam 3 and removing signals corresponding to the gas concentration.

In the above-mentioned fourth embodiment, when gas-sensitive film 36 is formed, sensor surface 7 may be omitted and gas-sensitive film 36 may be directly formed on the top surface of $SiO_2$ film 6.

In addition, in the light scanning type two-dimensional concentration distribution measuring equipment of the fourth embodiment as well, in place of moving sensor portion 2 in the X and Y directions, a light irradiating portion scanning equipment may be installed at beam irradiating portion 4, and light irradiating portion 4 may be moved in the X and Y directions. Alternatively, a light beam scanning equipment may be installed between beam irradiating portion 4 and sensor portion 2, and light beam 3 may be moved in the X and Y directions.

Furthermore, in the above-mentioned light scanning type two-dimensional concentration distribution measuring equipment, light beam 3 by beam irradiating portion 4 is designed to be irradiated from the side opposite to sensor surface 7 of semiconductor substrate 5. In place of this configuration, it may be irradiated from the side of sensor surface 7. For light irradiating portion 4, a light irradiating portion incorporated in semiconductor substrate 5 may be adopted as shown, for example, in Japanese Patent Application No. Hei 7-39114.

In the above-mentioned embodiment, changes of the two-dimensional distribution of ion concentration or gas concentration are designed to be detected, but the material evaluation method according to this invention is not limited to this but may be designed to detect the changes in distribution of compound concentration or further characteristic parameters such as oxidation-reduction potential.

The material evaluation method according to this invention can be applied not only to the evaluation of the above metal material but also to the evaluation of properties of bio-liquid of artificial bone material, corrosion resistance of fitting for dentures, the degree of coating of the coating material, penetration characteristics of artificial film, ion exchangers, and other wide range of metal materials, organic materials, and inorganic materials.

According to the material evaluation method of this invention, it is possible to evaluate various materials more easily and more quickly than in the conventional methods. Since it is possible to evaluate various materials directly in conformity with the real substance, the material can be evaluated with high accuracy and high reliability. In addition, the material evaluation method of this invention requires only a small amount of the specimens and provides excellent reproducibility.

What is claimed is:

1. A method for making current measurements in electrolyte between a sensor and a bulk, solid material to be evaluated, said method comprising the steps of:

providing a sensor having a semiconductor substrate and a sensor surface;

providing a light source disposed in a spaced relationship with said semiconductor substrate of said sensor, said light source for radiating said sensor with a light beam;

introducing an electrolyte to contact said sensor surface, positioning the bulk, solid material to be evaluated to contact said electrolyte;

said electrolyte being disposed between the bulk, solid material and the sensor surface; and irradiating said sensor with said light beam to cause a change in a property of said semiconductor substrate.

2. The method for evaluating bulk, solid materials as set forth in claim 1 further comprising the steps of:

providing a counter electrode between the bulk, solid material and said sensor surface; and providing a reference electrode between the bulk, solid material and said sensor surface.

3. The method for evaluating bulk, solid materials as set forth in claim 2, said providing a counter electrode step comprises facing said counter electrode towards said sensor surface, and said providing a reference electrode step comprises facing said reference electrode towards said sensor surface.

4. The method for evaluating solid materials as set forth in claim 1, wherein the bulk, solid material has a flat surface facing said sensor surface;

said positioning step comprises the step of positioning the flat surface of the bulk, solid material substantially parallel to the sensor surface.

5. The method for evaluating bulk, solid materials as set forth in claim 4, wherein said positioning step comprises positioning the flat surface of the bulk, solid material at a predetermined distance from the sensor surface.

6. The method for evaluating solid materials as set forth in claim 5, wherein the predetermined distance being about 1 mm.

7. The method for evaluating bulk, solid materials as set forth in claim 1, wherein the bulk, solid material is metallic.

8. The method for evaluating solid materials as set forth in claim 1, wherein the bulk, solid material is metallic and electrochemical reaction occurs at a portion where corrosion is formed, resulting in a localized change in the pH of the electrolyte;

said irradiating step comprises the step of irradiating said sensor with said light beam to measure the localized change in pH of said electrolyte.

9. The method for evaluating bulk, solid materials as set forth in claim 1, wherein said electrolyte is a gelled solution.

10. The method for evaluating bulk, solid materials as set forth in claim 9, wherein said gelled solution is an agar film.

* * * * *

UNITED STATES PATENT AND TRADEMARK OFFICE
CERTIFICATE OF CORRECTION

PATENT NO. : 6,053,035
DATED : April 25, 2000
INVENTOR(S) : Satoshi Nomura, Shuji Takamatsu, Motoi Nakao It is certified that error appears in the above-identified patent and that said Letters Patent is hereby corrected as shown below:

<u>Title page,</u>
Insert the Assignee as follows:
Horiba, Ltd., Kyoto, Japan

Signed and Sealed this

Twentieth Day of November, 2001

Attest:

*Nicholas P. Godici*

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO.    : 6,053,035
DATED         : April 25, 2000
INVENTOR(S)   : Satoshi Nomura, Shuji Takamatsu and Motoi Nakao It is certified that error appears in the above-identified patent and that said Letters Patent is hereby corrected as shown below:

<u>Title page,</u>
Item [73], please list the Assignees as follows:
-- Horiba, Ltd., Kyoto, Japan
   Research Institute of Innovative Technology for the Earth, Kyoto, Japan --

Signed and Sealed this

Twenty-fourth Day of December, 2002

JAMES E. ROGAN
*Director of the United States Patent and Trademark Office*